United States Patent
Greenawalt et al.

(10) Patent No.: US 11,549,884 B2
(45) Date of Patent: Jan. 10, 2023

(54) ZINC AND COPPER MEASUREMENT

(71) Applicant: Hach Company, Loveland, CO (US)

(72) Inventors: Angella Nicholle Greenawalt, Fort Collins, CO (US); Brendan Easley Young, Fort Collins, CO (US); Melanie Ann Roth, Loveland, CO (US)

(73) Assignee: HACH COMPANY, Loveland, CO (US)

(*) Notice: Subject to any disclaimer, the term of this patent is extended or adjusted under 35 U.S.C. 154(b) by 297 days.

(21) Appl. No.: 17/020,154

(22) Filed: Sep. 14, 2020

(65) Prior Publication Data

US 2022/0082493 A1    Mar. 17, 2022

(51) Int. Cl.
| | | |
|---|---|---|
| *G01N 21/31* | (2006.01) | |
| *G01N 1/28* | (2006.01) | |
| *G01N 33/18* | (2006.01) | |

(52) U.S. Cl.
CPC ............ *G01N 21/31* (2013.01); *G01N 1/28* (2013.01); *G01N 33/1813* (2013.01); *G01N 2001/2893* (2013.01); *G01N 2021/3125* (2013.01)

(58) Field of Classification Search
CPC .. G01N 33/182; G01N 33/1826; G01N 33/18; G01N 33/20; G01N 33/1813; G01N 31/005; G01N 31/22; G01N 21/78; G01N 21/643; G01N 21/31; G01N 2021/6439; G01N 2021/3125; G01N 1/28
USPC ...... 356/432–440; 436/182, 73, 77, 80, 106, 436/108, 119, 120, 164, 166, 175
See application file for complete search history.

(56) References Cited

U.S. PATENT DOCUMENTS

| | | | | |
|---|---|---|---|---|
| 4,533,642 | A * | 8/1985 | Kelly | ............... G01N 27/42 436/78 |
| 10,794,883 | B2 * | 10/2020 | Roth | ............... G01N 33/1813 |
| 10,890,574 | B2 * | 1/2021 | Greenawalt | ......... G01N 31/005 |
| 2021/0372924 | A1 | 12/2021 | Greenawalt | |

OTHER PUBLICATIONS

"Zinc—Test for Zinc in Natural and Treated Waters", Palintest Water Analysis Technologies, Phot.35.AUTO, V2-09/18, https://www.palintest.com/wp-content/uploads/2019/04/Phot.35.AUTO-Zinc-v2.pdf, 2 pages.
"Zinc, DOC316.53.01145,", Hach Company, Zinc, Zincon Method (3.00 mg/L), Jan. 2019, Edition 9; https://www.hach.com/asset-get.download-en.jsa?id=7639983910, pp. 1-6.

* cited by examiner

*Primary Examiner* — Hoa Q Pham
(74) *Attorney, Agent, or Firm* — Ference & Associates LLC

(57) ABSTRACT

An embodiment provides a method for measuring zinc and copper in an aqueous sample, including: reducing an aqueous sample containing an amount of zinc and an amount of copper with a reducing agent; buffering the reduced aqueous sample; chelating the amount of copper in the buffered aqueous sample with a copper(I) chelating agent; measuring the amount of copper in the aqueous sample by measuring a first change in intensity of the absorbance of the copper chelated aqueous sample; chelating the amount of zinc in the buffered aqueous sample with a zinc(II) chelating agent; and measuring the amount of zinc in the aqueous sample by measuring a second change in intensity of the absorbance of the zinc chelated aqueous sample. Other aspects are described and claimed.

20 Claims, 5 Drawing Sheets

| [Zn] (mg/L) in vial | average absorbance, 620 nm (N=7) | standard deviation |
|---|---|---|
| 0.00 | 0.048 | 0.002 |
| 0.117 | 0.079 | 0.001 |
| 1.00 | 0.378 | 0.001 |
| 3.50 | 1.20 | 0.024 |
| 5.83 | 1.88 | 0.003 |

| [Zn] (mg/L) in vial | Average absorbance, Chemkey (N=8) | Standard deviation |
|---|---|---|
| 0.00 | 0.023 | 0.002 |
| 0.10 | 0.039 | 0.003 |
| 1.00 | 0.162 | 0.004 |
| 3.00 | 0.436 | 0.009 |
| 5.00 | 0.734 | 0.018 |

ZINC AND COPPER MEASUREMENT

BACKGROUND

This application relates generally to measuring zinc and copper in aqueous or liquid samples.

Ensuring water quality is critical in a number of industries such as pharmaceuticals and other manufacturing fields. Additionally, ensuring water quality is critical to the health and well-being of humans, animals, and plants which are reliant on the water for survival. Metals such as copper and zinc may be measured and monitored. Too much copper or zinc in water can be harmful to humans or animals. For example, Copper and zinc may have long-term health effects and may cause the water to be less desirable to consumers or facilities. Copper or zinc may be present from natural or human activities such as manufacturing. Measurement and mitigation of copper and zinc may result in higher costs of water treatment. Therefore, detecting the presence and concentration of copper and/or zinc in water or other liquid solutions is vital.

BRIEF SUMMARY

In summary, one embodiment provides a method for measuring zinc and copper in an aqueous sample, comprising: reducing an aqueous sample containing an amount of zinc and an amount of copper with a reducing agent; buffering the reduced aqueous sample; chelating the amount of copper in the buffered aqueous sample with a copper(I) chelating agent; measuring the amount of copper in the aqueous sample by measuring a first change in intensity of the absorbance of the copper chelated aqueous sample; chelating the amount of zinc in the buffered aqueous sample with a zinc(II) chelating agent; and measuring the amount of zinc in the aqueous sample by measuring a second change in intensity of the absorbance of the zinc chelated aqueous sample.

Another embodiment provides a measurement device for measuring zinc and copper in an aqueous sample, comprising: a processor; and a memory storing instructions executable by the processor to: reduce an aqueous sample containing an amount of zinc and an amount of copper with a reducing agent; buffer the reduced aqueous sample; chelate the amount of copper in the buffered aqueous sample with a copper(I) chelating agent; measure the amount of copper in the aqueous sample by measuring a first change in intensity of the absorbance of the copper chelated aqueous sample; chelate the amount of zinc in the buffered aqueous sample with a zinc(II) chelating agent; and measure the amount of zinc in the aqueous sample by measuring a second change in intensity of the absorbance of the zinc chelated aqueous sample.

A further embodiment provides a method for measuring zinc and copper in an aqueous sample, comprising: reducing an aqueous sample containing an amount of zinc and an amount of copper with a reducing agent; buffering the reduced aqueous sample with Tris(hydroxymethyl)aminomethane; chelating the amount of copper in the buffered aqueous sample with bicinchoninic acid; measuring the amount of copper in the aqueous sample by measuring a first change in intensity of the absorbance of the copper chelated aqueous sample; chelating the amount of zinc in the buffered aqueous sample with 2-Carboxy-2'-hydroxy-5'-sulfoformazyl-benzene monosodium salt; and measuring the amount of zinc in the aqueous sample by measuring a second change in intensity of the absorbance of the zinc chelated aqueous sample.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
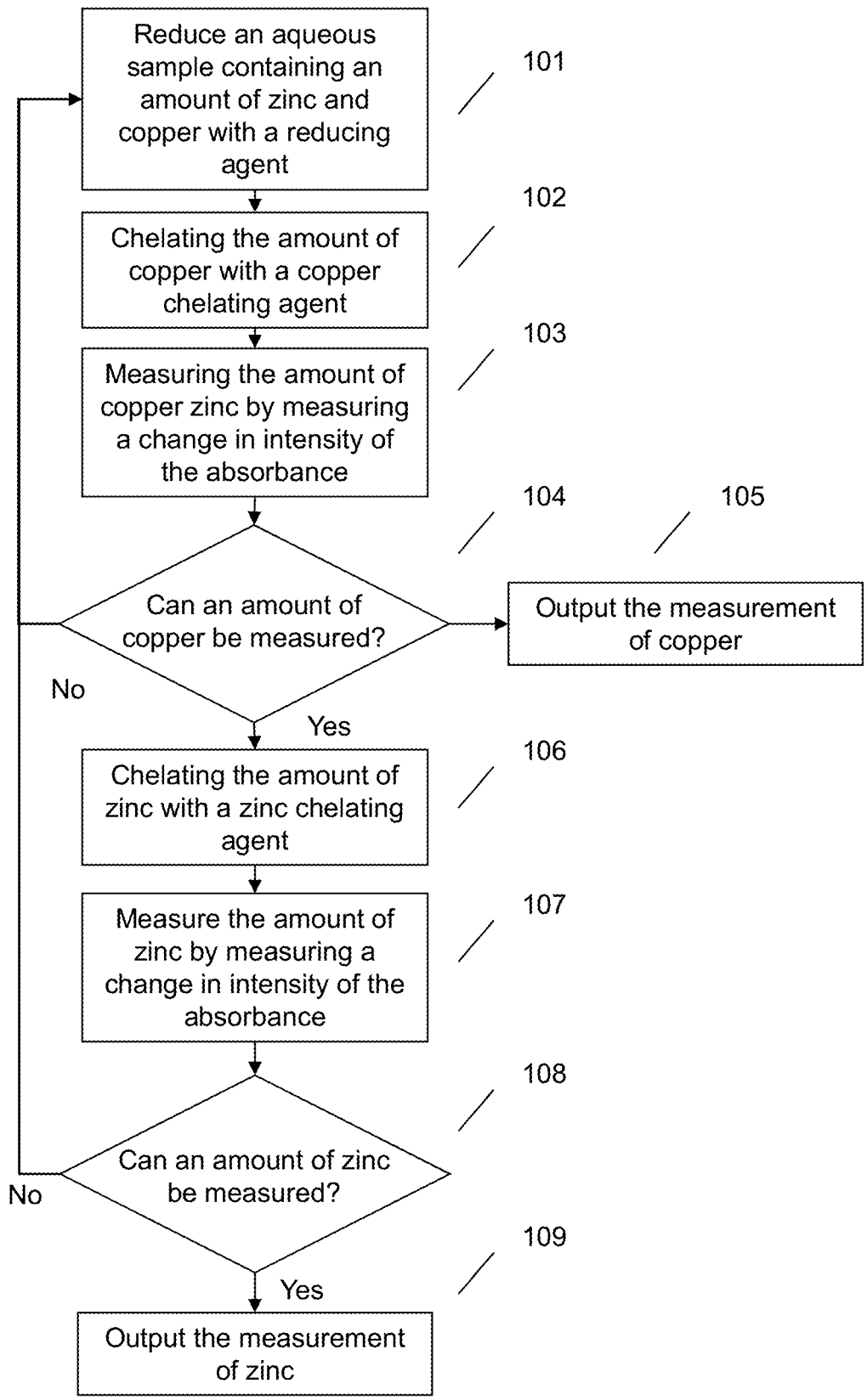
FIG. 1 illustrates a flow diagram of an example copper and zinc measuring system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Copper or zinc measurement in water or other aqueous samples or solutions is important for many different reasons. For example, copper or zinc measurement may be used to determine the quality of water. High concentrations of copper or zinc may be harmful to animals, humans, and/or plants. Accordingly, as another example, a user or entity may want the copper or zinc in a body of water to be under a particular threshold, therefore, the user may measure the copper or zinc in order to determine if the amount of copper or zinc is under that threshold. Copper or zinc may be present in a body of water either naturally or from human activity such as manufacturing or storage conditions.

Conventional methods of zinc measurement and detection may have limitations discussed herein. For example, conventional methods may use cyanide, cyclohexanone, and/or chloral hydrate. Governments may have limits of use or waste disposal requirements for these conventional methods. One example method is the Hach 8009-Zincon method. This method may detect zinc (Zn(II)) in the 0.010-3.0 mg/L range. The method has approximately a 3.5 minute reaction time, and uses either a spectrophotometer (620 nm) or colorimeter (610 nm) for measurement. However, there are some limitations with this method. First, the presence of excess indicator may interfere with a visual check. Second, there may be problem using this method in the presence of interferences above a given concentration. For example, aluminum above 6 mg/L, cadmium above 0.5 mg/L, iron (III) above 7 mg/L, manganese above 5 mg/L, and nickel above 5 mg/L may interfere with proper zinc measurement. The above noted interference levels and interference types are merely illustrative and may include other concentrations and/or interferences, for example, calcium and magnesium. Third, the method uses hazardous reagents such as cyanide and/or cyclohexanone.

Another example method for zinc measurement is the LCK 360-4-(2-pyridylazo)resorcinol method. This method detects zinc (Zn(II)) in the 0.2-6.0 mg/L range or 0.24-7.2 mg/L with Crack-Set LCW 902. The method has approximately a 3.0 minute reaction time. However, there are some limitations with this method. First, the method is for a very small sample size, such as 0.2 mL. Second, there may be problem using this method in the presence of interferences. Interferences include sulfate, chloride, sodium, potassium, calcium, nitrate, magnesium, iron(II and III), tin, nickel, copper, chromium, carbonate, cobalt, and/or lead. Third, the method uses hazardous reagents such as cyanide and/or chloral hydrate. The chloral hydrate may be especially problematic due to being on a list as a controlled substance in the United States.

A further example of zinc measurement is the Zinc Palintest method. The method reacts zinc with 2-Carboxy-2'-hydroxy-5'-sulfoformazyl-benzene monosodium salt (Zincon) in an alkaline solution resulting in an orange to blue color based on the zinc concentration. The color produced is indicative of the zinc concentration and is measured using a Palintest Photometer. Copper reacts in a similar manner to zinc and a correction procedure using ethylenediaminetetraacetic acid (EDTA) is applied to those samples which contain both zinc and copper. EDTA destroys the color complex formed with zinc. This is considered a bleaching method for zinc detection which is unfavorable.

Current methods, systems and kits for zinc measurement using the above methods using a spectrophotometric test or colorimetric test are limited because hazardous reagents are required to mitigate interferants, all of which have to potential to introduce significant errors in zinc measurements. Additionally, hazardous or controlled reagents make obtaining the reagents and disposal difficult. Also, the Palintest uses 2-Carboxy-2'-hydroxy-5'-sulfoformazyl-benzene monosodium salt to detect both zinc(II) and copper(II). However, the test measures zinc(II) and copper(II) (if present) and then uses EDTA to chelate zinc(II) and leave only the copper(II)-2-Carboxy-2'-hydroxy-5'-sulfoformazyl-benzene monosodium salt complex present. What is needed is an accurate method to measure copper and zinc in a water sample with fewer interference concerns and less hazardous reagents.

Additionally, the conventional methods use a bleaching chemistry not favorable to some uses and measurement systems. Additionally, the traditional colorimetric methods may require the preparation of a separate "blank" vial. The extra step of preparing a blank vial can introduce error to the measurement based upon individual human techniques in preparing the blank. Also, since the traditional colorimetric technique involves the bleaching of a dye, the time for preparation and time a measurement is taken, can introduce variability in the sample reading. Additionally, because the techniques include bleaching of a dye, difficulty may arise because there may not be the same volume of starting colorimetric dye in both the blank and sample vial, thereby introducing error into the determination of the amount of analyte found in the sample. This error may result in erroneous measurement of analytes.

Accordingly, an embodiment provides a system and method for measuring copper and zinc at low concentrations. In an embodiment, hazardous reagents such as cyanide are not used. In an embodiment, the colorimetric detection method does not use bleaching chemistry. In an embodiment, a colorimetric method may be used to measure copper and/or zinc in an aqueous sample or solution. The aqueous sample may contain an amount of copper and/or zinc to be measured. The aqueous sample may be reduced. The reducing agent may be sodium ascorbate. The aqueous sample may be buffered. The buffering may be to a pH at or around a pH of 8.2. The aqueous sample may be chelated. In an embodiment, a copper(I) chelating agent and/or a zinc(II) chelating agent may be used. The copper (I) chelating agent may be bicinchoninic acid. In an embodiment the zinc(II) chelating agent may be 2-Carboxy-2'-hydroxy-5'-sulfoformazyl-benzene monosodium salt (zincon). In an embodiment, an amount of copper may be measured in response to the copper(I) chelating agent. In an embodiment, the amount of copper in an aqueous sample may be measured by measuring a change in intensity of the absorbance of the copper chelated aqueous sample. In an embodiment, change in intensity of the absorbance is proportional to a concentration of the amount of copper in the aqueous sample. In an embodiment, an amount of zinc may be measured in response to the zinc(II) chelating agent. In an embodiment, the amount of zinc in an aqueous sample may be measured by measuring a change in intensity of the absorbance of the zinc chelated aqueous sample. In an embodiment, change in intensity of the absorbance is proportional to a concentration of the amount of zinc in the aqueous sample. In an embodiment, the chelating and measurement of copper and zinc may occur in a sequential manner. In an embodiment, the reducing agent, copper(I) chelating agent, and the zinc(II) chelating agent are introduced to the aqueous sample in a form selected from the group consisting of: a solution, a powder, and a prepackaged module, such as a CHEMKEY prepackaged module available from Hach Company, Loveland Colo., USA (CHEMKEY is a registered trademark of Hach Company in the United States and other countries). In an embodiment, the aqueous sample may comprise interferences, which may include: aluminum, copper, iron, manganese, calcium, magnesium, or the like. In an embodiment, the aqueous sample may be a sample of water for quality testing. The method may use a dual colorimetric method, for example, for the copper and the zinc measurement. In an embodiment, the method may proceed in the following order: reduction/buffering, copper chelation, copper measurement, zinc chelation, and zinc measurement.

The illustrated example embodiments will be best understood by reference to the figures. The following description is intended only by way of example, and simply illustrates certain example embodiments.

Referring to FIG. 1, an example system and method for measurement of copper and zinc in an aqueous sample or solution is illustrated. In an embodiment, a reducing agent may be prepared. The reducing agent may be introduced to a solution containing copper and zinc. In an embodiment, the reduced aqueous sample may be pH adjusted. In an embodiment, a copper(I) chelating agent may be added to the buffered aqueous sample. In an embodiment, a zinc chelating agent may be added to the buffered aqueous sample. Since different concentrations of copper and zinc result in different colorimetric intensities after respective chelation, the change in the colorimetric intensity may be correlated to a concentration of copper and zinc in the aqueous sample.

Figure 2:
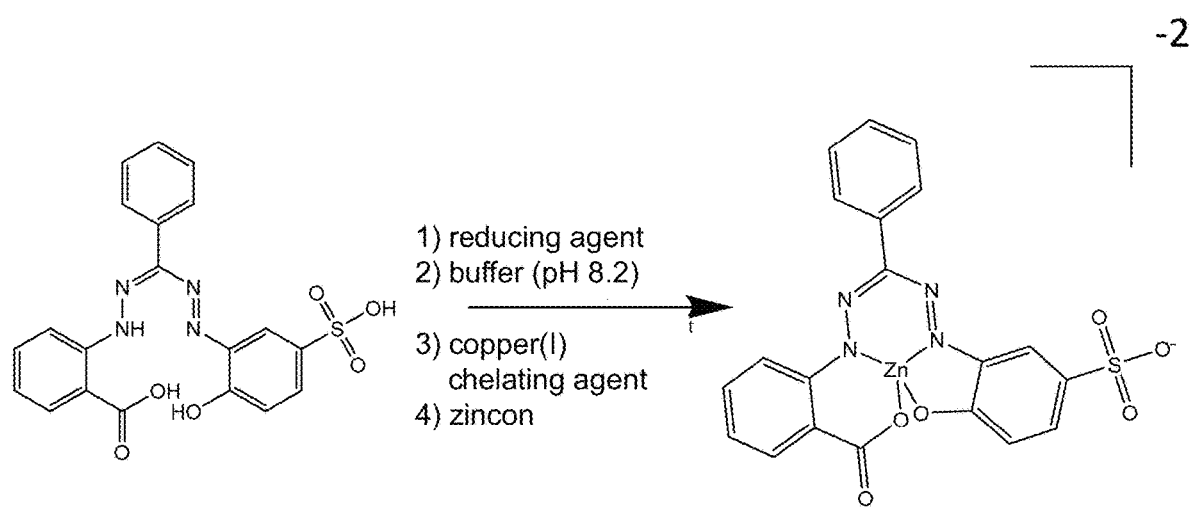
FIG. 2 illustrates a reaction scheme of an embodiment for detection of copper and zinc.

At 101, in an embodiment, a reducing agent may be prepared. The reducing agent may be sodium ascorbate (See FIG. 2). In an embodiment, the reducing agent may be placed in a solution, aqueous sample, water sample or the like. The reducing agent may be added to a chamber, vessel, or the like as a powder, a liquid, or a prepackaged module such as a CHEMKEY prepackaged module. The reducing agent may be added manually or using an autonomous system.

In an embodiment, aqueous sample may be buffered. The buffering may occur after the addition of the reducing reagent. The resultant pH may be to about equal to, above, or below a pH of 8.2 (See FIG. 2). The buffer or buffer agent may be Tris(hydroxymethyl)aminomethane. In an embodiment, a pH value may be selected to minimize interferences. For example, a pH may be selected based upon the concentration and/or composition of interferences. Possible interferences may include aluminum, copper, iron, manganese, calcium, magnesium, or the like. An aqueous sample may have may contain one of more interferences of varying concentration, or no interferents at all.

The aqueous sample may include a sample from a natural body of water, a holding tank, a processing tank, a pipe, or the like. The solution may be in a continuous flow, a standing volume of liquid, or any combination thereof. In one embodiment, the solution may be introduced to the reducing agent or buffer, for example, a test chamber of the measurement device. In an embodiment, the measurement device may be a benchtop, field, or hand held device. A hand held device may have advantages such as lower cost, portability, field use, or the like. Introduction of the solution into the measurement device may include placing or introducing the solution into a test chamber manually by a user or using a mechanical means, for example, gravity flow, a pump, pressure, fluid flow, or the like. For example, a water sample for copper and zinc measurement may be introduced to a measurement or test chamber using a pump. In an embodiment, valves or the like may control the influx and efflux of the solution into or out of the one or more chambers, if present.

A chamber, vessel, cell, chamber, or the like may contain an aqueous sample and associated reagents such as reducing agent, buffering agent, copper chelating, and/or zinc chelating agent. Various reagents may be added to an aqueous sample in the form of a powder, a liquid, a prepackaged module such as a CHEMKEY prepackaged module, or the like. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample with reducing agent, buffering agent, copper chelating, and/or zinc chelating agent.

Additionally or alternatively, the measurement device may be present or introduced in a volume of the solution. The measurement device may then be exposed to the volume of an aqueous sample where it may perform measurements. The system may be a flow-through system in which an aqueous sample and/or reagents are automatically mixed and measured. Once the sample is in contact with the measurement system, the system may measure the copper and zinc of the sample, as discussed in further detail herein. In an embodiment, the measurement device may include one or more chambers in which the one or more method steps may be performed.

At 102, in an embodiment, a copper chelating agent may be added to the aqueous sample. The copper chelating agent may be added after the reducing agent and/or the buffering. In an embodiment, the copper chelating agent may be a copper(I) chelating agent (See FIG. 2). The copper(I) chelating agent may be bicinchoninic acid. The copper chelating agent may be added to a chamber, vessel, or measurement chamber. The copper chelating agent may be added in a measured amount using manual or autonomous methods to correspond to the volume of the aqueous sample containing copper. In an embodiment, the use of bicinchoninic acid instead of ethylenediaminetetraacetic acid (EDTA) allows for the simultaneous mitigation and measurement of a copper interference in the aqueous sample.

At 103, in an embodiment, the system and method may measure an amount of copper in the solution by measuring a change in the intensity of the absorbance caused by the copper reacting with the copper(I) chelating agent. In an embodiment, the presence of copper in an aqueous solution may cause an increase in absorbance intensity. Thus, the change in absorbance of the solution may be proportional to the amount of copper within the solution. The method may replace EDTA with bicinchoninic acid to both remove copper interference from zinc measurement, while allowing measurement of both the copper and zinc amount in the aqueous sample, an improvement over conventional methods. Accordingly, a measurement device or user can correlate the measured change in absorbance with the amount of copper in the aqueous sample.

Therefore, the absorbance intensity, of an aqueous sample containing copper may be correlated to the concentration of the copper in the aqueous solution. In an embodiment, the amount of absorbance may be proportional to an amount or concentration of zinc in the solution. Absorbance curves may be generated for a range of copper concentrations, for any different condition that may affect absorption or absorbance values (e.g., temperature, sample content, turbidity, viscosity, measurement apparatus, aqueous sample chamber, etc.), or the like. The absorbance curves can then be used for determining the amount of copper in the solution.

At 104, in an embodiment, the system and method may determine if an amount of copper may be measured. For example, an amount of copper may be measured using colorimetric methods. The absorbance measurements may be compared to expected values, historical values, or the like. Copper measurement using colorimetric methods may be at periodic intervals set by the user or preprogrammed frequencies in the device. Measurement of copper by a device allows for real time data with very little human involvement in the measurement process. In the event that the system outputs an unexpected value, the system may automatically request re-measurement of a solution or sample.

A programmed calibration curve may be entered into the device for calibrating the measurement device. In an embodiment, the system and method may be periodically tested using a known amount of copper in the sample. The system may then recalibrate or send an error report for maintenance. In the event that the error is caused by an unclean device or that the device otherwise needs cleaned, the system may implement a cleaning cycle. Cleaning of the colorimetric chamber may be required at an unspecified time interval, after a certain number of measurements, upon user or system request, or the like. In an embodiment, a cleaning cycle of the colorimetric device may be performed using either automated or manual methods.

At 104, in an embodiment, if a concentration of copper cannot be determined, the system may continue to measure copper and/or an absorbance signal. Additionally or alternatively, the system may output an alarm, log an event, or the like. If a concentration of copper can be determined, the system may provide a measurement of copper concentration at 105. The measurement which may be the absorbance intensity or copper concentration may be an output that is provided to a device in the form of a display, printing, storage, audio, haptic feedback, or the like. Alternatively or additionally, the output may be sent to another device through wired, wireless, fiber optic, Bluetooth®, near field communication, or the like.

An embodiment may use an alarm to warn of a measurement or concentration outside acceptable levels. An embodiment may use a system to shut down water output or shunt water from sources with unacceptable levels of copper. For example, a copper measuring device may use a relay coupled to an electrically actuated valve, or the like. The system may connect to a communication network. The system may alert a user or a network. This alert may occur whether a copper measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a copper concentration reaches a threshold. Alarms or logs may be analyzed in real-time, stored for later use, or any combination thereof.

At 106, in an embodiment, a zinc chelating agent may be added to the aqueous sample. The zinc chelating agent may be added after the reducing agent and/or the buffering. The zinc chelating agent may be added after the copper chelating agent is added to the aqueous sample and a copper measurement. In an embodiment, the zinc chelating agent may be a zinc(II) chelating agent (See FIG. 2). The zinc(II) chelating agent may be 2-Carboxy-2'-hydroxy-5'-sulfoformazyl-benzene monosodium salt (zincon). The zinc chelating agent may be added to a chamber, vessel, or measurement chamber. The zinc chelating agent may be added in a measured amount using manual or autonomous methods to correspond to the volume of the aqueous sample containing zinc.

At 107, in an embodiment, the system and method may measure an amount of zinc in the solution by measuring a change in the intensity of the absorbance caused by the zinc reacting with the zinc(II) chelating agent. In an embodiment, the presence of zinc in an aqueous solution may cause an increase in absorbance intensity. Thus, the change in absorbance of the solution may be proportional to the amount of zinc within the solution.

Figures 3A, 3B:
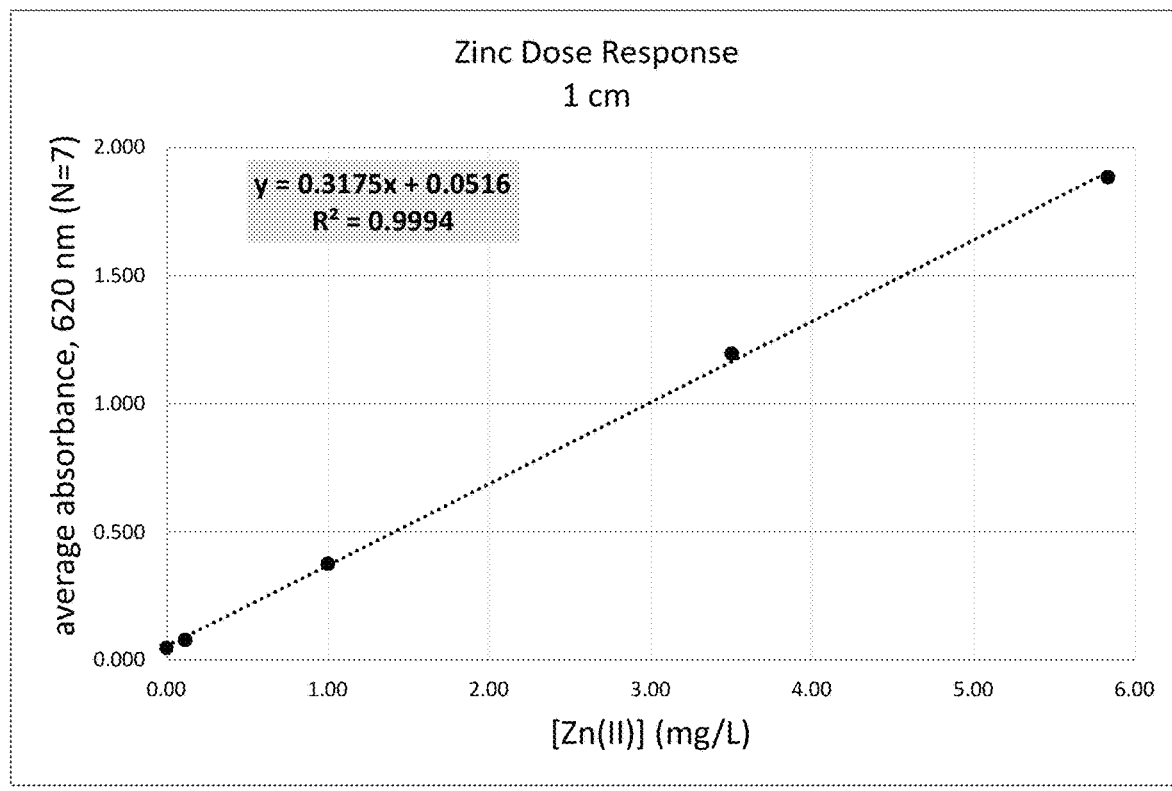
FIG. 3A illustrates the average absorbance plotted against the zinc concentration and an example absorbance curve for a 2-Carboxy-2'-hydroxy-5'-sulfoformazyl-benzene monosodium salt (zincon) method.
FIG. 3B illustrates the data from FIG. 3A in a table form.
Figures 4A, 4B:
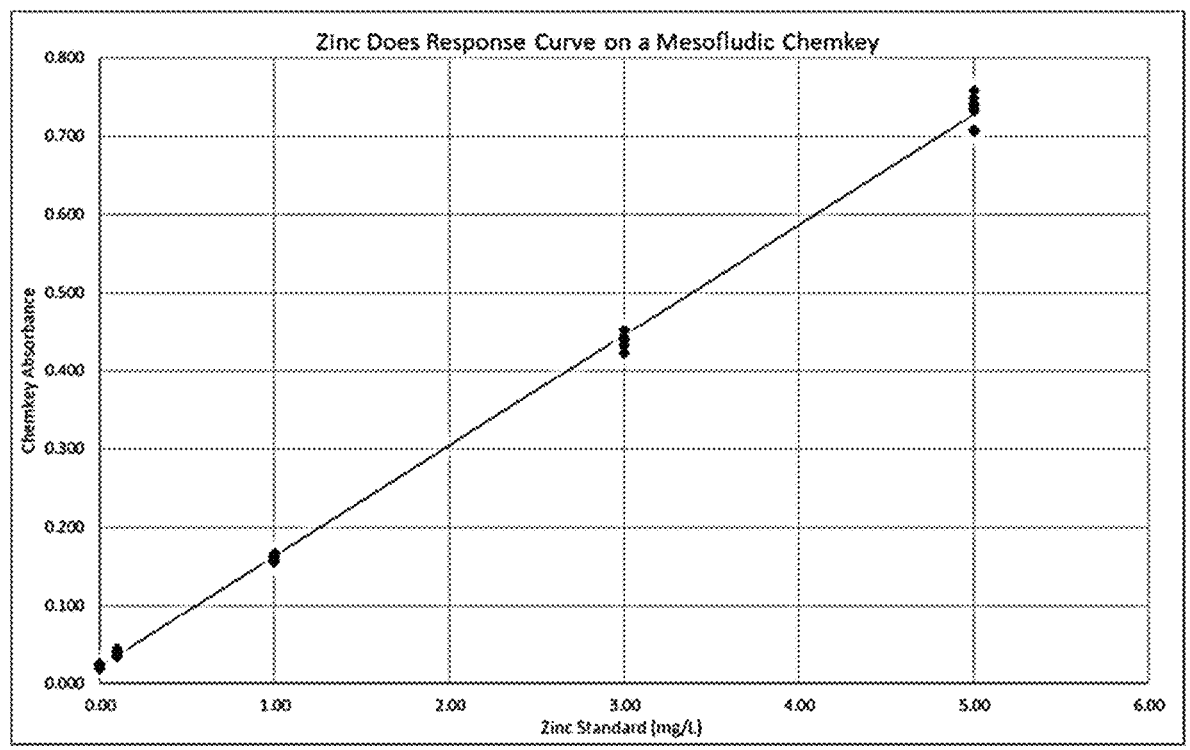
FIG. 4A illustrates the average absorbance plotted against the zinc concentration and an example absorbance curve for a mesofluidic method.
FIG. 4B illustrates the data from FIG. 4A in a table form.

Absorbance may be measured using different methods. For example, the measurement may be made in a vial using an absorbance of about 620 nm. Example absorbance data are illustrated in FIG. 3 A-B in which the average absorbance is plotted against the zinc concentration and an example absorbance curve for a 2-Carboxy-2'-hydroxy-5'-sulfoformazyl-benzene monosodium salt (zincon) method, and also presented in a table form. As another example, the absorbance measurement may be performed using a micro or mesofluidic device, such as a "lab on a chip" type device. Example absorbance data on a mesofluidic CHEMKEY prepackaged module are illustrated in FIG. 4 A-B, and also presented in a table form. Accordingly, a measurement device or user can correlate the measured change in absorbance with the amount of zinc in the aqueous sample.

Therefore, the absorbance intensity, of an aqueous sample containing zinc may be correlated to the concentration of the zinc in the aqueous solution. In an embodiment, the amount of absorbance may be proportional to an amount or concentration of zinc in the solution. Absorbance curves may be generated for a range of zinc concentrations, for any different condition that may affect absorption or absorbance values (e.g., temperature, sample content, turbidity, viscosity, measurement apparatus, aqueous sample chamber, etc.), or the like. The absorbance curves can then be used for determining the amount of zinc in the solution.

At 108, in an embodiment, the system and method may determine if an amount of zinc may be measured. For example, an amount of zinc may be measured using colorimetric methods. The colorimetric measurements may be compared to expected values, historical values, or the like. Zinc measurement using colorimetric methods may be at periodic intervals set by the user or preprogrammed frequencies in the device. Measurement of zinc by a device allows for real time data with very little human involvement in the measurement process. In the event that the system outputs an unexpected value, the system may automatically request re-measurement of a solution or sample.

A programmed calibration curve may be entered into the device for calibrating the measurement device. In an embodiment, the system and method may be periodically tested using a known amount of zinc in the sample. The system may then recalibrate or send an error report for maintenance. In the event that the error is caused by an unclean device or that the device otherwise needs cleaned, the system may implement a cleaning cycle. Cleaning of the colorimetric chamber may be required at an unspecified time interval, after a certain number of measurements, upon user or system request, or the like. In an embodiment, a cleaning cycle of the colorimetric device may be performed using either automated or manual methods.

At 108, in an embodiment, if a concentration of zinc cannot be determined, the system may continue to measure zinc and/or an absorbance signal. Additionally or alternatively, the system may output an alarm, log an event, or the like. If a concentration of zinc can be determined, the system may provide a measurement of copper concentration at 109. The measurement which may be the absorbance intensity or zinc concentration may be an output that is provided to a device in the form of a display, printing, storage, audio, haptic feedback, or the like. Alternatively or additionally, the output may be sent to another device through wired, wireless, fiber optic, Bluetooth®, near field communication, or the like.

An embodiment may use an alarm to warn of a measurement or concentration outside acceptable levels. An embodiment may use a system to shut down water output or shunt water from sources with unacceptable levels of zinc. For example, a zinc measuring device may use a relay coupled to an electrically actuated valve, or the like. The system may connect to a communication network. The system may alert a user or a network. This alert may occur whether a zinc measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a zinc concentration reaches a threshold. Alarms or logs may be analyzed in real-time, stored for later use, or any combination thereof.

The various embodiments described herein thus represent a technical improvement to conventional copper and zinc measurement techniques. Using the techniques as described herein, an embodiment may use a colorimetric indicator to measure copper and zinc in solution. This is in contrast to the use of cyanide and/or bleaching chemistry with limitations mentioned above. Such techniques provide a faster and more accurate method for measuring copper and zinc in an aqueous or liquid solution, while using less dangerous or harmful chemicals or reagents in the copper and zinc measurement.

Figure 5:
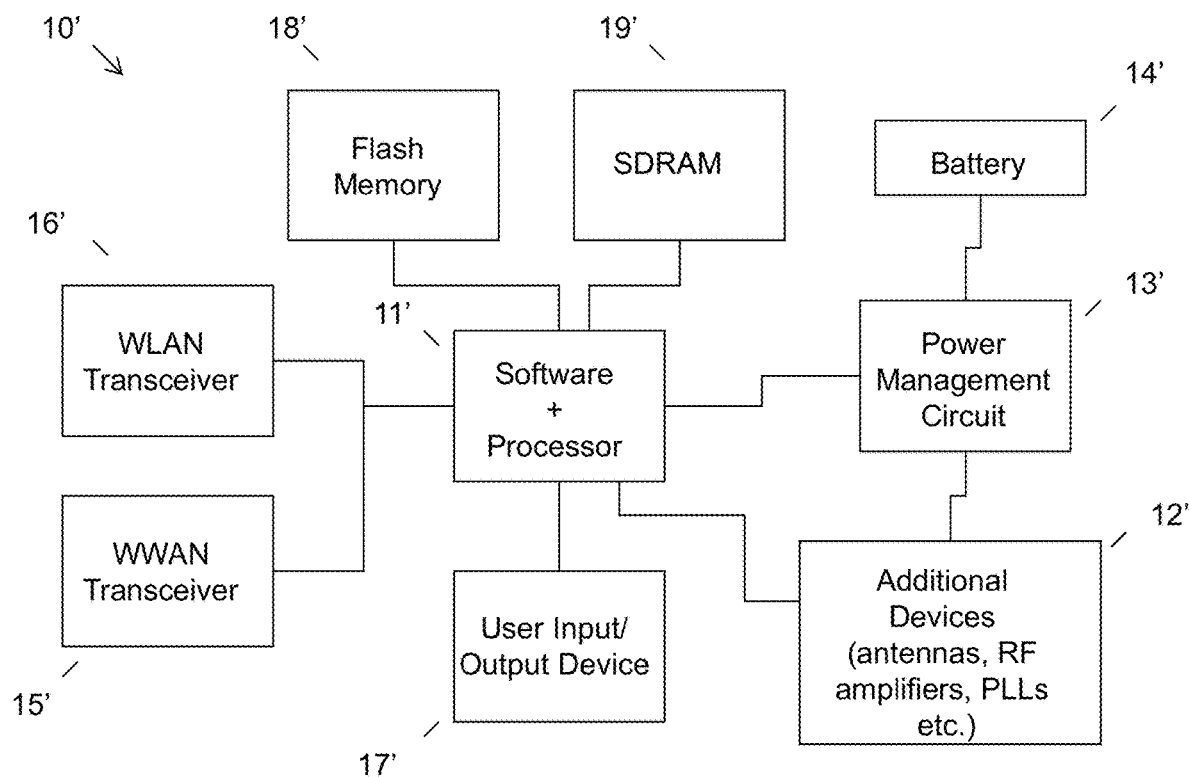
FIG. 5 illustrates an example of computer circuitry.

While various other circuits, circuitry or components may be utilized in information handling devices, regarding an instrument for measurement of copper and zinc according to any one of the various embodiments described herein, an example is illustrated in FIG. 5. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of copper and zinc of an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring zinc and copper in an aqueous sample, comprising:
    reducing an aqueous sample containing an amount of zinc and an amount of copper with a reducing agent;
    buffering the reduced aqueous sample;
    chelating the amount of copper in the buffered aqueous sample with a copper(I) chelating agent;
    measuring the amount of copper in the aqueous sample by measuring a first change in intensity of the absorbance of the copper chelated aqueous sample;
    chelating the amount of zinc in the buffered aqueous sample with a zinc(II) chelating agent; and
    measuring the amount of zinc in the aqueous sample by measuring a second change in intensity of the absorbance of the zinc chelated aqueous sample.

2. The method of claim 1, wherein the reducing agent comprises sodium ascorbate.

3. The method of claim 1, wherein the buffer comprises Tris(hydroxymethyl)aminomethane.

4. The method of claim 1, wherein the copper(I) chelating agent comprises bicinchoninic acid.

5. The method of claim 1, wherein the first change in intensity of the absorbance is proportional to a concentration of the amount of copper in the aqueous sample.

6. The method of claim 1, wherein the zinc(II) chelating agent comprises 2-Carboxy-2'-hydroxy-5'-sulfoformazyl-benzene monosodium salt.

7. The method of claim 1, wherein the second change in intensity of the absorbance is proportional to a concentration of the amount of zinc in the aqueous sample.

8. The method of claim 1, wherein the reducing agent, buffer, copper(I) chelating agent, and the zinc(II) chelating agent are introduced to the aqueous sample in a form selected from the group consisting of: a solution, a powder, and a prepackaged module.

9. The method of claim 1, wherein the aqueous sample further comprises interferences.

10. The method of claim 1, wherein the aqueous sample comprises a water sample for quality testing.

11. A measurement device for measuring zinc and copper in an aqueous sample, comprising:
    a processor; and
    a memory storing instructions executable by the processor to:
        reduce an aqueous sample containing an amount of zinc and an amount of copper with a reducing agent;
        buffer the reduced aqueous sample;
        chelate the amount of copper in the buffered aqueous sample with a copper(I) chelating agent;
        measure the amount of copper in the aqueous sample by measuring a first change in intensity of the absorbance of the copper chelated aqueous sample;
        chelate the amount of zinc in the buffered aqueous sample with a zinc(II) chelating agent; and
        measure the amount of zinc in the aqueous sample by measuring a second change in intensity of the absorbance of the zinc chelated aqueous sample.

12. The device of claim 11, wherein the reducing agent comprises sodium ascorbate.

13. The device of claim 11, wherein the buffer comprises Tris(hydroxymethyl)aminomethane.

14. The device of claim 11, wherein the copper(I) chelating agent comprises bicinchoninic acid.

15. The device of claim 11, wherein the first change in intensity of the absorbance is proportional to a concentration of the amount of copper in the aqueous sample.

16. The device of claim 11, wherein the zinc(II) chelating agent comprises 2-Carboxy-2'-hydroxy-5'-sulfoformazyl-benzene monosodium salt.

17. The device of claim 11, wherein the second change in intensity of the absorbance is proportional to a concentration of the amount of zinc in the aqueous sample.

18. The device of claim 11, wherein the reducing agent, buffer, copper(I) chelating agent, and the zinc(II) chelating agent are introduced to the aqueous sample in a form selected from the group consisting of: a solution, a powder, and a prepackaged module.

19. The device of claim 11, wherein the aqueous sample further comprises interferences.

20. A method for measuring zinc and copper in an aqueous sample, comprising:
    reducing an aqueous sample containing an amount of zinc and an amount of copper with a reducing agent;
    buffering the reduced aqueous sample with Tris(hydroxymethyl)aminomethane;
    chelating the amount of copper in the buffered aqueous sample with bicinchoninic acid;
    measuring the amount of copper in the aqueous sample by measuring a first change in intensity of the absorbance of the copper chelated aqueous sample;
    chelating the amount of zinc in the buffered aqueous sample with 2-Carboxy-2'-hydroxy-5'-sulfoformazyl-benzene monosodium salt; and
    measuring the amount of zinc in the aqueous sample by measuring a second change in intensity of the absorbance of the zinc chelated aqueous sample.

* * * * *